United States Patent [19]

Doherty et al.

[11] 3,963,734

[45] June 15, 1976

[54] LOWER ALKYLSULFONYL 2-AMINO, 3-NITRO PYRIDINES

[75] Inventors: George O. P. Doherty, Greenfield, Ind.; Kenneth H. Fuhr, Columbus, Ohio

[73] Assignee: Eli Lilly and Company, Indianapolis, Ind.

[22] Filed: Feb. 15, 1974

[21] Appl. No.: 443,075

Related U.S. Application Data

[60] Division of Ser. No. 181,574, Sept. 17, 1971, Pat. No. 3,813,408, which is a continuation-in-part of Ser. No. 21,535, March 20, 1970, abandoned.

[52] U.S. Cl. .......................................... 260/294.8 F
[51] Int. Cl.$^2$ ........................................ C07D 213/71
[58] Field of Search ................. 260/294.8 F, 294.8 G

[56] References Cited
UNITED STATES PATENTS

| | | | |
|---|---|---|---|
| 3,409,624 | 11/1968 | De Selms | 260/294.8 F |
| 3,470,172 | 9/1969 | Kaufman | 260/294.8 F |
| 3,547,935 | 12/1970 | Diehl et al. | 260/294.8 G |

OTHER PUBLICATIONS

Forrest et al. "Chem. Abstracts" vol. 43 (1949) p. 1995d.

Takahashi et al. "Chem. Abstracts" vol. 44 (1950) p. 7320d.

Takahashi et al. "Chem. Abstracts" vol. 50 (1956) pp. 1000i–1001.

Semonsky et al. "Chem. Abstracts" vol. 50 (1956) p. 3438g.

Montgomery et al. "Chem. Abstracts" vol. 64, (1966) p. 19745b.

*Primary Examiner*—Henry R. Jiles
*Assistant Examiner*—R. W. Ramsuer
*Attorney, Agent, or Firm*—Kathleen R. S. Page; Everet F. Smith

[57] ABSTRACT

Substituted 1-hydroxy-2-(1,1-difluoroalkyl)-1H-imidazo-(4,5-*b*)pyridine compounds useful as herbicides; and intermediates useful in the synthesis of these compounds. In addition to exhibiting herbicidal activity, the substituted 1-hydroxy-2-(1,1-difluoroalkyl)-1H-imidazo(4,5-b)pyridine compounds are of low mammalian toxicity.

5 Claims, No Drawings

LOWER ALKYLSULFONYL 2-AMINO, 3-NITRO PYRIDINES

CROSS-REFERENCE TO RELATED APPLICATIONS

This is a division of copending application Ser. No. 181,574, filed Sept. 17, 1971 and issued May 28, 1974 as U.S. Pat. No. 3,813,408. Application Ser. No. 181,574 was in turn a continuation-in-part of copending application Ser. No. 21,535, filed Mar. 20, 1970 and abandoned after the filing of application Ser. No. 181,574.

SUMMARY OF THE INVENTION

The present invention is directed to substituted-1-hydroxy-2-(1,1-difluoroalkyl)-1H-imidazo(4,5-b) pyridine compounds of the following formula:

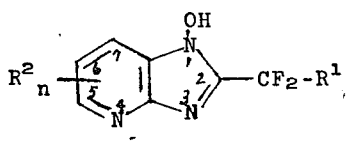

and the salts thereof. In the above and succeeding formulae throughout the present specification and claims, $R^1$ represents hydrogen, chlorine, fluorine, difluoromethyl, perfluoroalkyl of $C_1$-$C_6$, or radical of the formula

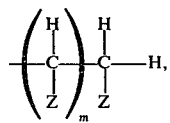

wherein each Z independently represents hydrogen or halogen and m represents 0 or 1; $R^2$ represents amino, halogen, nitro, cyano, loweralkyl of $C_1$-$C_4$, perfluoroalkyl of $C_1$-$C_8$, -$CF_2Cl$, -$CF_2H$, or loweralkylsulfonyl of $C_1$-$C_4$; and n represents an integer of from 1 to 3, both inclusive, subject to the limitations (1) that all $R^2$ substituents together contain not more than 8 carbon atoms; (2) that not more than two $R^2$ symbols represent loweralkylsulfonyl groups; and (3) that where two loweralkylsulfonyl groups are present, they are located at the 5- and 7-positions. These compounds are useful as herbicides. Hence, the present invention is also directed to methods employing and compositions comprising the compounds as herbicides. The above-described compounds are also useful as starting materials from which other of the above-described compounds can be prepared.

In addition, the present invention is also directed to various separate classes of intermediates useful in the preparation of the compounds defined above, including the most intermediate precursors of the formulae:

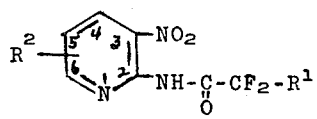

wherein $R^1$ and $R^2$ are as defined above, and

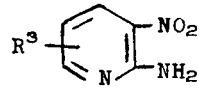

wherein $R^3$ represents loweralkylsulfonyl of $C_1$-$C_4$, both inclusive.

DETAILED DESCRIPTION OF THE INVENTION

In the present specification and claims, the term "halogen" is employed to designate bromine, chlorine, fluorine, and iodine, only.

An essential and distinguishing structural feature of the compounds of the present invention is the substituent at the 2 position (—$CF_2$—$R^1$); representative such radicals include the following:
difluoromethyl
trifluoromethyl
difluorochloromethyl
pentafluoroethyl
heptafluoro-n-propyl
1,1-difluoroethyl
1,1-difluoro-n-propyl
1,1-difluoro-2-bromoethyl
1,1-difluoro-2-chloroethyl
1,1-difluoro-2,3-dichloro-n-propyl
1,1-difluoro-3-bromo-n-propyl
1,1,2-trifluoroethyl
1,1,2-trifluoro-n-propyl
1,1,2,3-tetrafluoro-n-propyl
1,1-difluoro-2-bromo-3-chloro-n-propyl
perfluoro-n-butyl
perfluoro-n-pentyl
perfluoro-n-hexyl
1,1,2,2-tetrafluoroethyl Preferred groups are trifluoromethyl, difluoromethyl, difluorochloromethyl, 1,1,2,2-tetrafluoroethyl, and pentafluoroethyl.

The compounds of the present invention are typically crystalline solids. Two synthetic routes are useful in the preparation of the compounds. The first of these is as follows:

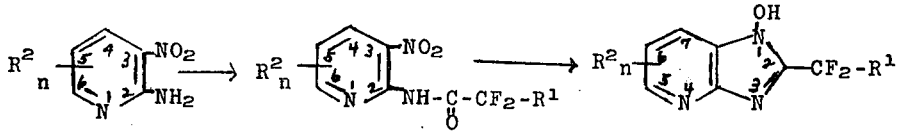

In accordance with the foregoing reaction route, the initial substituted-2-amino-3-nitropyridine compound is acylated to yield the corresponding substituted-2-(2,2-difluoroalkanamido)-3-nitropyridine, which is then reacted further to yield the final product in accordance with the present invention. Because of the ready availability of suitable starting materials, this reaction scheme is particularly suited to the preparation of the mono-substituted compounds of the present invention. Where suitable starting materials are available, it is equally suited to the preparation of di- and tri-substituted compounds. However, the di- and tri-substituted compounds are often preferably prepared in an alternate synthetic route, discussed below.

In the synthetic route described above, the acylation is carried out with an acylating agent, the identity of which is not critical; either the difluoroalkanoyl halide:

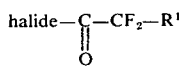

or the difluoroalkanoic anhydride

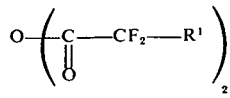

is suitable, although the latter is often preferred. In general, the reaction is conducted by mixing the acylating agent and the substituted-3-nitro-2-aminopyridine. In the case of a difluoroalkanoyl halide, the use of an acid accepting amide or organic tertiary amine is preferred. Particularly suited organic tertiary amines include triethylamine and pyridine; and suitable amides include DMF and dimethylacetamide. The reaction goes forward at temperatures of from 25°–100°C. and can be conducted in an inert liquid reaction medium, such as benzene; or an excess of the organic tertiary amine can be employed as reaction medium; in addition, the difluoroalkanoic anhydrides are generally liquid, and an excess amount can be used to assure fluidity. The reaction goes forward readily yielding the desired substituted-3-nitro-2-(2,2-difluoroalkanamido)pyridine product. Separation of the product, and, if desired, purification are carried out in conventional procedures.

The reaction of the resulting substituted-3-nitro-2-(2,2-difluoroalkanamido)pyridine to prepare the ultimate products of the present invention, is in part the subject of copending application Ser. No. 21,226, filed Mar. 19, 1970. In general, it has been found that subjecting the substituted-3-nitro-2-(2,2-difluoroalkanamido)pyridine compounds, as well as other compounds, to any of a variety of reducing conditions results in the preparation of the ultimate substituted-1-hydroxy-2-(1,1-difluoroalkyl)-1H-imidazo(4,5-b)pyridine compounds of the present invention. It is believed that the reaction proceeds through an intermediate:

conditions ordinarily employed for the reduction of nitro compounds to amino compounds: hydrogen in the presence of a catalyst; zinc or iron in acid solution; sulfides in alkaline solution; hydrosulfite in alkaline solution; and the like. The reactions are conducted in accordance with the conditions known for each of these agents (see Kirk-Othmer Encyclopedia of Chemical Technology, 2nd Ed., Vol. 2, pages 76–98 and references there cited [John Wiley and Sons, Inc., 1963, New York]); and in all instances, cyclodehydration of the intermediate occurs spontaneously under such reducing conditions.

However, a preferred method for conducting the reduction reaction is the use of hydrogen in the presence of a catalyst. In general, in employing this preferred method, the substituted-3-nitro-2-(2,2-difluoroalkanamido)pyridine, conveniently in an inert liquid as reaction medium, is subjected to hydrogenation in the presence of catalyst, typically a noble metal and preferably palladium or platinum. The catalyst can be employed alone, or -- especially in the instance of palladium--can be supported on a carrier such as carbon or an alkali metal salt. Conveniently, a Parr or other pressure apparatus is used to contain the reaction mixture during hydrogenation, when conducted at superatmospheric pressures; however, the reaction also goes forward at atmospheric pressures. The reaction is further catalyzed by a small amount of an acid, such as, for example, a mineral acid such as hydrochloric acid or a compatible organic acid such as trifluoroacetic acid.

The amounts of reactants employed are not critical. In general, preferred amounts are 2 moles of hydrogen per mole of the starting substituted-3-nitro-2-(2,2-difluoroalkanamido)pyridine and a catalytic amount of the noble metal, such as from 1 to 10 grams per kilogram of the starting compound. Temperatures of from 0° to 100°C. are operative, but better results are typically achieved at temperatures of from 10° to 25°C.

When hydrogen uptake is complete, the product is separated from the reaction mixture in conventional procedures. Most typically, the reaction mixture is filtered to remove remaining catalyst, and the filtrate evaporated to separate the product as a residue. This product residue can be purified, also in conventional procedures, typically recrystallization, or extraction into sodium bicarbonate solution followed by precipitation with mineral acid.

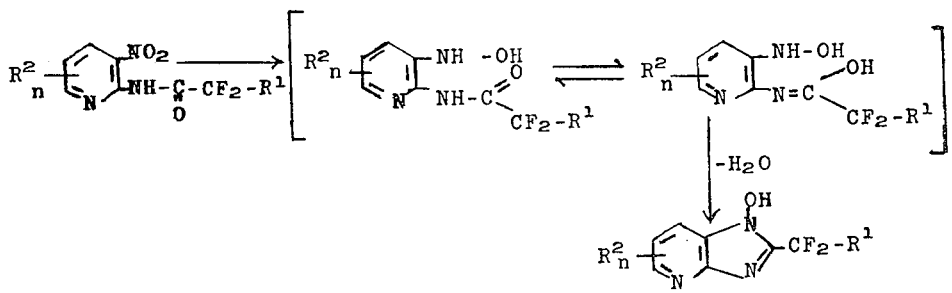

To date, it has not been possible to isolate this intermediate. As will be obvious to those skilled in the art, however, the intermediate, if isolatable from any synthetic route, could itself be reacted to produce the compounds of the present invention.

While the reaction itself is unexpected, the reaction conditions are not critical. As reducing agent, there can be employed, for example, any of the substances and In an alternate synthetic route, a suitably substituted 1-hydroxy compound of the present invention is itself used as a starting material for the preparation of other of the compounds of the present invention. This synthetic route is particularly suited to the preparation of the poly substituted compounds of the present invention ($n = 2$ or 3) where the necessary starting material for the first synthetic route is not readily available. The 1-hydroxy compound is subjected to reactions to introduce onto the pyridine ring one or more desired groups and/or to convert one or more substituents already present on the pyridine ring to the desired group or groups.

Thus, for example, the 1-hydroxy compound serving as starting material for this synthetic route can be halogenated or nitrated at a position or positions previously unsubstituted. A nitro group already present can be reduced to an amino group; and an amino group already present can also be oxidized back to a nitro group. An amino group can also be diazotized and replaced by, for example, a halo group, a nitrile group, or a loweralkylthio group. Oxidation of the loweralkylthio-substituted compound yields the corresponding loweralkylsulfonyl-substituted compound. The fluorinated groups ($R^2 = -CF_3$, $-CF_2Cl$, or $-CF_2H$) are readily obtained, initially by conversion of a nitrile to a carboxyl group; subsequent treatment with $SF_4$ in the presence of HF yields the $-CF_3$ group. Alternately, conversion to an aldehyde and treatment with $SF_4$ alone yields the $-CF_2H$ group; and subsequent chlorination converts the $-CF_2H$ group to the corresponding $-CF_2Cl$ group. An alkyl substituent is introduced by reaction of an alkyl lithium with a halo-substituted 1-hydroxy compound; and a perfluoroalkyl substituent is introduced by reaction of a halo-substituted 1-hydroxy compound with a perfluoroalkyl iodide in the presence of copper. This and numerous other conversion and substitution reactions are well known to those skilled in the art. Attention is directed to Fieser and Fieser, Advanced Organic Chemistry (Reinhold Publishing Corp., New York, N.Y., 1961), especially chapters 9 and 17. See also Wagner and Zook, Synthetic Organic Chemistry (John Wiley and Sons, Inc., New York, N.Y., 1953).

As will be understood by those skilled in the art, more than one of the foregoing reactions will be needed to complete the preparation of some of the compounds of the present invention; and in the case of all reactions, due consideration must be given to the orienting effect of substituent groups. Also, for those of the foregoing reactions which utilize a nucleophilic reagent, it may be necessary that the 1-hydroxy group be converted to an ester or ether. Conversion is readily achieved by reacting the 1-hydroxy compound with an alkyl halide or an acyl halide in the presence of a hydrogen chloride acceptor. The identity of the alkyl halide or acyl halide is not critical: suitable compounds include the methyl halides and the acetyl halides. An ester derivative is converted back to the 1-hydroxy compound in conventional procedures.

The foregoing synthetic methods result in the preparation of the desired substituted-1-hydroxy-2-(1,1-difluoroalkyl)-1H-imidazo(4,5-b)pyridine compounds of the present invention. However, the proton of the OH group being acidic, these compounds form salts with cations. Representative such salts include salts with alkali metals, such as sodium, potassium, lithium, cesium, and rubidium; alkaline earth metal salts, such as calcium, strontium, and barium salts; and salts with organic amines. While the identity of the organic amine is not critical, preferred organic amines are those which have relatively high base strength, such as a dissociation constant ($K_b$) of the order of $10^{-5}$ or greater. In general, the alkylamines, cycloalkylamines, alkylenepolyamines, and aralkylamines are classes of compounds exhibiting adequate base strengths. Thus, representative bases include methylamine, dimethylamine, trimethylamine, methyldiethylamine, ethylamine, diethylamine, triethylamine, n-propylamine, di-n-propylamine, tri-n-propylamine, n-amylamine, cyclohexylamine, piperidine, pyrrolidine, N-methylpyrrolidine, diisopropylamine, ethylenediamine, tetramethylenediamine, ethanolamine, benzylamine, isobutylamine, di-n-butylamine, and the like. The foregoing salts are prepared in conventional procedures, by reaction of the 6-substituted-1-hydroxy-2-(1,1-difluoroalkyl)imidazo(4,5-b)pyridine and the particular amine or alkali metal or alkaline earth metal oxide, hydroxide, or salt. Such salt formation can be employed as a method of formulating the subject compounds.

The following examples illustrate the present invention and will enable those skilled in the art to practice the same.

EXAMPLE 1:
5-CHLORO-3-NITRO-2-(TRI-FLUOROACETAMIDO)PYRIDINE

5-Chloro-3-nitro-2-aminopyridine (5.0 grams) and excess trifluoroacetic anhydride were refluxed together for 24 hours. TLC showed no reaction had taken place. Pyridine (2.0 ml.) was then added. After fifteen minutes the solution solidified. The product was dissolved in chloroform and washed twice with water, and the chloroform was then evaporated under vacuum. The resulting product residue was recrystallized from a mixture of benzene and aliphatic naphtha: m.p., 104°–05°C., yield 6.0 g.

Analysis, Calc.: C, 31.20; H, 1.12; N, 15.59.
Found: C, 32.20; H, 1.44; N, 15.83.

EXAMPLE 2:
5-CHLORO-3-NITRO-2-(TRI-FLUOROACETAMIDO)PYRIDINE

The compound of Example 1 was also synthesized by dissolving the 5-chloro-3-nitro-2-aminopyridine (5.0 grams) in a minimum amount of warm trifluoroacetic acid, and then adding 1.5 equivalents of trifluoroacetic anhydride and 0.5 milliliters of pyridine and refluxing for about an hour. The reaction mixture was then poured onto ice to precipitate the 5-chloro-3-nitro-2-(trifluoroacetamido)pyridine compound, which was separated, dissolved in chloroform, and washed twice with water. Thereafter, the solution was shaken with activated carbon and filtered, and chloroform removed under vacuum to obtain a purified product. It was further recrystallized from a low boiling (40°–50°C.) petroleum ether, m.p., 104°–05°C.

EXAMPLE 3:
5-(TRIFLUOROMETHYL)-3-NITRO-2-(TRI-FLUOROACETAMIDO)-PYRIDINE 5-(Trifluoromethyl)-3-nitro-2-aminopyridine (2.0 grams) was mixed with 10 milliliters of pyridine and 1 milliliter of trifluoroacetic anhydride added with cooling. After 30 minutes, the reaction mixture was heated to 100°C. and maintained thereat for 10 minutes. The reaction mixture was then poured into ice and hydrochloric acid (of a concentration of 50 grams of ice per 10 milliliters of hydrochloric acid). The reaction mixture was then filtered and the resulting residue, the desired 5-(trifluoromethyl)-3-nitro-2-(trifluoroacetamido)pyridine, taken up in chloroform, dried, and solvent evaporated to obtain a purified product. It was further recrystallized from benzene, m.p., 68°–70°C.

EXAMPLE 4:
5-(METHYLSULFONYL)-3-NITRO-2-(TRIFLUOROACETAIDO)-PYRIDINE 5-(Methylsulfonyl)-3-nitro-2-aminopyridine (2.0 grams) was mixed with 15 milliliters of trifluoroacetic anhydride and 4 milliliters of pyridine. The resulting mixture was stirred under reflux until the reaction mixture changed color, from gray to dark brown, and began solidifying. An additional 10 milliliters of the trifluoroacetic anhydride was then added and the reaction mixture refluxed for another hour. The excess anhydride was then removed by evaporation, yielding the desired 5-(methylsulfonyl)-3-nitro-2-(trifluoroacetamido)pyridine. It was dissolved in chloroform, washed once with water, and dried over magnesium sulfate; the chloroform was then removed by evaporation, and the resulting product was recrystalized from benzene/acetone, m.p., 159°–61°C.

Analysis, Calc.: C, 30.67; H, 1.93; N, 13.42.
Found: C, 30.73; H, 2.00; N, 13.58.

EXAMPLE 5:
1-HYDROXY-2,6-BIS(TRIFLUOROMETHYL)-1H-IMIDAZO-(4,5-b)PYRIDINE 5-(Trifluoromethyl)-3-nitro-2-aminopyridine (10.0 grams) in trifluoroacetic anhydride (10 ml.) and pyridine (20 ml.) were heated in a steam bath for two hours. Solvents were then evaporated on a rotary evaporator at 100°C. for one hour, and the residue was taken up in ethyl acetate and hydrogenated over 2.0 g. of 5 percent palladium on carbon. The reaction mixture was then filtered, evaporated, and taken up in ethanol; subsequently, the mixture was washed with 10 percent hydrochloric acid, dried over magnesium sulfate, and evaporated. The resulting 1-hydroxy-2,6-bis(-trifluoromethyl)-1H-imidazo(4,5-b)pyridine product was recrystallized from acetone, m.p., 239°–40°C.

Analysis, Calc.: C, 35.44; H, 1.15 ; N, 15.50; F, 42.05.
Found: C, 35.40; H, 1.43; N, 15.28; F, 42.32.

EXAMPLE 6: 6-CHLORO-1-HYDROXY-2-(TRIFLUOROMETHYL)-1H-IMIDAZO(4,5-b) PYRIDINE 5-chloro-3-nitro-2-(trifluroracetamido)pyridine (2.0 grams) was hydrogenated with two moles of hydrogen in ethanol containing 0.5 gram of 5 percent palladium on carbon. The resulting reaction mixture was filtered and evaporated to separate the desired 6-chloro-1-hydroxy-2-(trifluoromethyl)-1H-imidazo(4,5-b)pyridine compound which, after recrystallization from benzene melted at 268°–70°C.

Analysis, Calc.: C, 35.39; H, 1.27; N, 17.69.
Found: C, 35.59; H, 1.45; N, 17.77.

EXAMPLE 7:
6-CHLORO-1-HYDROXY-2-(TRIFLUOROMETHYL)IMIDAZO(4,5-b)-PYRIDINE

5-Chloro-3-nitro-2-(trifluoroacetamido)pyridine (2.7 grams), anhydrous stannous chloride (3.8 grams), and 4.0 milliliters of concentrated hydrochloric acid were mixed in 20 milliliters of acetic acid. The mixture was cooled to temperatures of 0°–10°C. and maintained thereat for 15 minutes. Water (50 milliliters) was then added to the reaction mixture, and the desired 6-chloro-1-hydroxy-2-(trifluoromethyl)imidazo(4,5-b)-pyridine product precipitated. It was separared and dried. The yield was 1.3 grams, 55 percent. The product so obtained melted at 264°–66°C.

EXAMPLE 8:
6-CHLORO-1-HYDROXY-2-(TRIFLUOROMETHYL)-1H-IMIDAZO(4,5-b)PYRIDINE TRIETHYLAMINE SALT

6-Chloro-1-hydroxy-2-(trifluoromethyl)-1H-imidazo(4,5-b)-pyridine (1 gram) was mixed with 15 milliliters of tetrahydrofuran, and 0.7 milliliter of triethylamine added. The reaction mixture was evaporated and then held in a vacuum desiccator overnight, resulting in the desired 6-chloro-1-hydroxy-2-(trifluoromethyl)-1H-imidazo(4,5-b)pyridine triethylamine salt. The compound was subjected to NMR analysis (in deuterium oxide); analysis showed a triplet centered at 82 cps (9H); a quartet centered at 196 cps (6H); a meta-coupled doublet at 400 cps (1H); and a second metacoupled doubled centered at 503 cps (1H).

EXAMPLE 9:
6-CHLORO-1-HYDROXY-2-(TRIFLUOROMETHYL)-1H-IMIDAZO(4,5-b) PYRIDINE BENZYLAMINE SALT

6-CHLORO-1-hydroxy-2-(Trifluoromethyl)-1H-imidazo(4,5-b)-pyridine (1.4 grams) was mixed with 15 milliliters of ethyl acetate. The mixture was heated to reflux, and 0.6 milliliter of benzylamine was added dropwise. The mixture was then refluxed for another 30 minutes, cooled, and filtered, yielding the desired 6-chloro-1-hydroxy-2-(trifluoromethyl)-1H-imidazo(4,5-b)pyridine benzylamine salt, m.p., 200°–02°C. NMR analysis in hexadeuterodimethyl sulfoxide showed a peak at 236 cps (2H); a peak at 437 cps (5H); two meta-coupled doublets at the 462 cps (1H), the other at 500 cps (1H); and a broad peak at 474 cps (3H).

Analysis, Calc.: C, 48,75; H, 3.51; N, 16.25.
Found: C, 48,52; H, 3.72; N, 16.07.

EXAMPLE 10:
6-AMINO-1-HYDROXY-2-(TRIFLUOROMETHYL)-1H-IMIDAZO-(4,5-b)PYRIDINE

6-Nitro-1-hydroxy-2-(trifluoromethyl)-1H-imidazo(4,5-b)- pyridne (4.9 grams) was mixed with 100 milliliters of ethanol and 3 milliliters of concentrated hydrochloric acid, and 1 gram of 5 percent palladium on carbon was added to the mixture. The mixture was hydrogenated to a 3 mole-equivalent uptake of hydrogen. The reaction mixture was then filtered and evaporated, yielding a gummy solid residue which was taken up in 150 milliliters of water and used directly in the reaction reported in the following example.

EXAMPLE 11:
5,7-DIBROMO-6-AMINO-1-HYDROXY-2-(TRIFLUOROMETHYL)-1H-IMIDAZO(4,5-b)PYRIDINE

The aqueous solution of 6-amino-1-hydroxy-2-(trifluoromethyl)-1H-imidazo(4,5-b)pyridine obtained as reported in the preceding example was treated with 2.2 milliliters of bromine in an $N_2$-$H_2O$ stream. Thereafter the reaction mixture was stirred for sixteen hours under nitrogen. The desired 5,7-dibromo-6-amino-1-hydroxy-2-(trifluoromethyl)-1H-imidazo(4.5-b)pyridine precipitated in the reaction mixture and was separated by filtration. It waa taken up in 250 milliliters of diethyl ether, stirred for one hour, dried over magnesium sulfate, and filtered. The diethyl ether was evaporated to give 3.4 grams of the desired product in purified form, m.p., 242°–4°C (dec.).

EXAMPLE 12:
5,7-DIBROMO-6-NITRO-1-HYDROXY-2-(TRIFLUOROMETHYL)-1H-IMIDAZO(4.5-b)PYRIDINE 5,7-Dibromo-6-amino-1-hydroxy-2-(trifluoromethyl)-1-H-imidazo(4,5-b)pyridine (25 milligrams) was added to a stirred solution of 2 milliliters of 30 percent hydrogen peroxide and 5 milliliters of sulfuric acid at about 5°C. The reaction mixture was allowed to come to 25°C. and permitted to stand for one hour. The reaction mixture was then diluted with ice water, extracted with diethyl ether, and dried over magnesium sulfate, and the ether evaporated leaving a residue, the desired 5,7-dibromo-6-nitro-1-hydroxy-2-(trifluoromethyl)-1H-imidazo(4,5-b)pyridine. It was recrystallized from chloroform, m.p., 204°C. (dec.).

EXAMPLE 13: DIAZONIUM SALT DERIVED FROM 1,5-DIHYDROXY-7-BROMO-6-DIAZO-2-(TRIFLUOROMETHYL)-1H-IMIDAZO(4,5-b)PYRIDINE 5,7-Dibromo-6-amino-1-hydroxy-2-(trifluoromethyl)-1H-imidazo(4,5-b)pyridine (1.2 grams) in 7 milliliters of concentrated hydrochloric acid was cooled with stirring to about 10°C. Sodium nitrite (0.35 gram) in 2.0 milliliters of water was then added dropwise with stirring and the reaction mixture was stirred at ambient temperature of about 25°C. for about sixteen and one-half hours. The reaction mixture was then diluted with water and filtered to separate a solid, the desired diazonium salt derived from 1,5-dihydroxy-7-bromo-6-diazo-2-(trifluoromethyl)-1H-imidazo(4,5-b)pyridine. It was promptly analyzed by IR, which showed a peak at 2.80, confirming the Nstretch, and a low (1630–1640) carbonyl absorption. The formula of this diazonium salt is as follows:

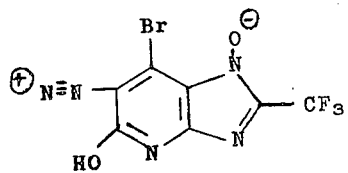

EXAMPLE 14:
5,7-DIBROMO-6-CHLORO-1-HYDROXY-2-(TRIFLUOROMETHYL)-1H-IMIDAZO(4,5-b)PYRIDINE 5,7-Dibromo-6-amino-1-hydroxy-2-(trifluoromethyl)-1H-imidazo(4,5-b)pyridine (1.2 grams) in 7 milliliters of concentrated HCl was cooled to 0°–10°C. Thereafter, sodium nitrite (0.35 gram) was added as a solid. The addition was carried out portionwise to maintain the temperature below 10°C. Five minutes after completion of the addition of the sodium nitrite, cuprous chloride (0.45 grams) was added portionwise and the resulting reaction mixture stirred for thirty minutes and filtered to separate the desired 5,7-dibromo-6-chloro-1-hydroxy-2-(trifluoromethyl)-1-H-imidazo(4,5-b)pyridine product, m.p. 215°C.

Analysis, Calc.: C, 21.27; H, 0.25; N, 10.63.
Found: C, 21.50; H, 0.50; N, 11.10.

EXAMPLES 15–47:

Other products of the present invention are prepared in accordance with the procedures and teachings hereinabove. Representative such other products include the following:

3,5-Dinitro-2-aminopyridine is reacted with difluoroacetic anhydride to obtain 3,5-dinitro-2-(difluoroacetamido)pyridine, which in turn is hydrogenated in the presence of platinum to obtain 6-nitro-1-hydroxy-2-(difluoromethyl)-1H-imidazo(4,5-b)-pyridine. 5-Bromo-3-nitro-2-aminopyridine is treated with chlorodifluoroacetic anhydride to yield 5-bromo-3-nitro-2-(chlorodifluoroacetamido)pyridine, which on hydrogenation in the presence of palladium on barium sulfate, yields 6-bromo-1-hydroxy-2-(chlorodifluoromethyl)-1H-imidazo(4,5-b)pyridine.

5-Ethylsulfonyl-3-nitro-2-aminopyridine is reacted with trifluoroacetic anhydride to obtain 5-ethylsulfonyl-3-nitro-2-(Trifluoroacetamido)pyridine, which on hydrogenation in the presence of palladium on carbon yields 6-ethylsulfonyl-1-hydroxy-2-(trifluoromethyl)-1H-imidazo(4,5-b)pyridine.

5-Chloro-3-nitro-2-aminopyridine is treated with pentafluoropropionic anhydride to obtain 5-chloro-3-nitro-2-(pentafluoropropionamido)pyridine, which when hydrogenated in the presence of palladium on carbon yields 6-chloro-1-hydroxy-2-(pentafluoroethyl)-1H-imidazo(4,5-b)pyridine, m.p., 240°–42°C.

5-(Chlorodifluoromethy)-3-nitro-2-aminopyridine is reacted with heptafluorobutyric anhydride to obtain 5-(chlorofifluoromethyl)-3-nitro-2-(heptafluorobutyramido)pyridine, which on hydrogenation in the presence of palladium on calcium sulfate yields 6-(chlorodifluoromethyl)-1-hydroxy-2-(heptafluoropropyl)-1H-imidazo(4,5-b)pyridine.

5-(n-Butylsulfonyl)-3-nitro-2-aminopyridine is reacted with trifluoroacetic anhydride to obtain 5-(n-butylsulfonyl)-3-nitro-2-(Trifluoroacetamido)pyridine, which on hydrogenation on the presence of platinum yields 6-(n-butylsulfonyl)-1-hydroxy-2-(trifluoromethyl)-1H-imidazo(4,5-b)pyridine.

5-(Difluoromethyl)-3-nitro-2-aminopyridine is reacted with difluoroacetic anhydride to obtain 5-(difluoromethyl)-3-nitro-2-(difluoroacetamido)pyridine, which when hydrogenated in the presence of palladium on barium sulfate yields 2,6-bis(difluoromethyl)-1-hydroxy-1H-imidazo(4,5-b)pyridine.

5-(Methylsulfonyl)-3-nitro-2-aminopyridine is reacted with trifluoroacetic anhydride to obtain 5-(methylsulfonyl)-3-nitro2-(trifluoroacetamido)pyridine which when hydrogenated yields 6-(methylsulfonyl)-1-hydroxy-2-(trifluoromethyl)-1H-imidazo(4,5-b)-pyridine, m.p., 265°–68°C.

Analysis, Calc: C, 34.17; H, 2.15; N, 14.94.
Found: C, 34.27; H, 2.37; N, 15.07.

5-Chloro-3-nitro-2-aminopyridine is reacted with heptafluorobutyric anhydride to obtain 5-chloro-3-nitro-2-(heptafluorobutyramido)pyridine which when hydrogenated yields 6-chloro-1-hydroxy-2-(heptafluoro-n-propyl)-1H-imidazo(4,5-b)-pyridine.

5-Chloro-3-nitro-2-aminopyridine is reacted with 2,2-difluoropropionic anhydride to obtain 5-chloro-3-nitro-2-(2,2-difluoropropionamido)pyridine, which on hydrogenation in the -dicarboxyl--bis-acid chloride gives the dialdehyde which is reacted with SF$_4$ to obtain 5,6-bis(difluoromethyl)-1-hydroxy-2 presence of palladium on calcium sulfate yield 6-chloro-1-hydroxy-2-(1,1-difluoroethyl)-1H-imidazo(4,5-b)pyridine.

5-(Trifluoromethyl)-3-nitro-2-aminopyridine is reacted with 2,2-difluoro-3-bromopropionic anhydride to obtain 5-(trifluoromethyl)-3-nitro-2-(2,2-difluoro-3-bromopropionamido)pyridine, which on hydrogenation in the presence of platinum yields 6-(trifluoromethyl)-1-hydroxy-2-(1,1-difluoro-2-bromoethyl)-1H-imidazo(4,5-b)pyridine.

5-Iodo-3-nitro-2-aminopyridine is reacted with 2,2-difluorobutyric anhydride to obtain 5-iodo-3-nitro-2-(2,2-difluorobutyramido)pyridine, which when hydrogenated in the presence of palladium on barium sulfate yields 6-iodo-1-hydroxy-2-(1,1-difluoro-n-propyl)-1H-imidazo(4,5-b)pyridine.

5-(Methylsulfonyl)-3-nitro-2-aminopyridine is reacted with 2,2-difluoro-3,4-dichlorobutyric anhydride to obtain 5-(methylsulfonyl)-3-nitro-2-(2,2-difluoro-3,4-dichlorobutyramido)pyridine which when hydrogenated yields 6-(methylsulfonyl)-1-hydroxy-2-(1,1-difluoro-2,3-dichloro-n-propyl)-1H-imidazo(4,5-$b$)-pyridine.

5-Fluoro-3-nitro-2-aminopyridine is reacted with 2,2,3-trifluoropropionic anhydride to obtain 5-fluoro-3-nitro-2-(2,2,3-trifluoropropionamido)pyridine which on hydrogenation over palladium on carbon yields 6-fluoro-1-hydroxy-2-(1,1,2-trifluoroethyl)-1H-imidazo(4,5-b)pyridine.

5-(Trifluoromethyl)-3-nitro-2-aminopyridine is reacted with 2,2-difluoro-4-iodobutyric anhydride to obtain 5-(trifluoromethyl)-3-nitro-2-(2,2-difluoro-4-iodobutyramido)pyridine, which on hydrogenation yields 6-(trifluoromethyl)-1-hydroxy-2-(1,1-difluoro-3-iodo-n-propyl)-1H-imidazo(4.5-b)pyridine.

5-Chloro-3-nitro-2-aminopyridine is reacted with perfluoroöctanoic anhydride to obtain 5-chloro-3-nitro-2-(2,2,3,3,4,4,5,5,6,6,7,7,8,8,8-pentafluorooctanamido)pyridine, which on hydrogenation yields 6-chloro-1-hydroxy-2-(perfluoro-n-heptyl)-1H-imidazo(4,5-b)pyridine. This compound is reacted with dimethylamine to obtain the dimethylamine salt thereof.

5-(Trifluoromethyl)-3-nitro-2-aminopyridine is reacted with perfluorobutyryl chloride to yield 5-(trifluoromethyl)-3-nitro-2-(2,2,3,3,4,4,4,-heptafluorobutyramido)pyridine, which when hydrogenated yields 6-(trifluoromethyl)-1-hydroxy-2-(perfluoro-n-propyl)-1H-imidazo(4,5-b)pyridine.

6-(Chlorodifluoromethyl)-1-hydroxy-2-(trifluoromethyl)-1H-imidazo(4,5-b)pyridine is reacted with pyridine to obtain the pyridine salt thereof.

6-(Methylsulfonyl)-1-hydroxy-2-(trifluoromethyl)-1H-imidazo(4,5-b)pyridine, in a dilute agueous solution of sodium hydroxide, forms the sodium salt thereof in solution.

6-Nitro-1-hydroxy-2-(trifluoromethyl)-1H-imidazo(4,5-b)-pyridine is reacted with an aqueous solution of calcium carbonate, yielding the calcium salt thereof.

6-Chloro-3-nitro-2-aminopyridine is reacted with trifluoroacetic anhydride to obtain 6-chloro-3-nitro-2-(trifluoroacetamido)pyridine, which when hydrogenated yields 5-chloro-1-hydroxy-2-(trifluoromethyl)-1H-imidazo(4,5-b)pyridine, m.p., 216°C. (dec.).

Analysis, Calc.: C, 35.39; H, 1.27; N, 17.69.

Found: C, 35.60; H, 1.48; N, 17.96.

4-Chloro-3-nitro-2-aminopyridine is reacted with trifluoroacetic anhydride to obtain 4-chloro-3-nitro-2-(trifluoroacetamido)pyridine, which when hydrogenated yields 7-chloro-1-hydroxy-2-(trifluoromethyl)-1H-imidazo(4,5-b)pyridine, m.p., 170°–1°C.

5-Chloro-1-hydroxy-2-(pentafluoroethyl)-1H-imidazo(4,5-b)-pyridine is reacted with methanethiol to obtain 5-(methylthio)-1-hydroxy-2-(pentafluoroethyl)-1H-imidazo(4,5-b)pyridine which is subsequently oxidized to obtain the corresponding 5-(methylsulfonyl)-1-hydroxy-2-(pentafluoroethyl)-1H-imidazo(4,5-b)-pyridine.

7-Chloro-1-hydroxy-2-(difluoromethyl)-1H-imidazo(4,5-b)-pyridine is reacted with sodium fluoride to obtain 7-fluoro-1-hydroxy-2-(difluoromethyl)-1H-imidazo(4,5-b)pyridine, which is then converted to its calcium salt.

5-Chloro-1-hydroxy-2-(1,1,2,2-tetrafluoroethyl)-1H-imidazo(4,5-b)pyridine is brominated to obtain 5-chloro-6-bromo-1-hydroxy-2-(1,1,2,2-tetrafluoroethyl)-1H-imidazo(4,5-b)pyridine, which is then converted to its sodium salt.

7-Chloro-1-hydroxy-2-(difluorochloromethyl)-1H-imidazo-(4,5-b)pyridine is reacted with ammonium hydroxide to obtain 7-amino-1-hydroxy-2-(difluorochloromethyl)-1H-imidazo(4,5-b)pyridine which is oxidized to the corresponding 7-nitro-1-hydroxy-2-(difluorochloromethyl)-1H-imidazo(4,5-b)pyridine. Also, the 7-amino-1-hydroxy-2-(difluorochloromethyl)-1H-imidazo(4,5-b)-pyridine is treated with sodium nitrite and subsequently sodium cyanide to obtain the corresponding 7-cyano-1-hydroxy-2-(difluorochloromethyl)-1H-imidazo(4,5-b)pyridine. On treatment with 70 percent sulphuric acid the corresponding 7-carboxy-1-hydroxy-2-(difluorochloromethyl)-1H-imidazo(4,5-b)pyridine is prepared. On further treatment with SF$_4$ and HF, there is obtained 7-(trifluoromethyl)-1-hydroxy-2-(difluorochloromethyl)-1H-imidazo(4,5-b)pyridine.

6-Amino-1-hydroxy-2-(trifluoromethyl)-1H-imidazo(4,5-b)-pyridine is nitrated to obtain 6-amino-5,7-dinitro-1-hydroxy-2-(trifluoromethyl)-1H-imidazo(4,5-b)pyridine which is subsequently oxidized to obtain the corresponding 5,6,7-trinitro-1-hydroxy-2-(trifluoromethyl)-1H-imidazo(4,5-b)pyridine.

6-Amino-1-hydroxy-2-(difluoromethyl)-1H-imidazo(4,5-b)-pyridine is chlorinated to obtain 6-amino-5,7-dichloro-1-hydroxy-2-(difluoromethyl)-1H-imidazo(4,5-b)pyridine. This compound is diazotized and treated with cuprous chloride to convert it to 5,6,7-trichloro-1-hydroxy-2-(difluoromethyl)-1H-imidazo(4,5-b)pyridine.

5,6-Diamino-1-hydroxy-2-(trifluoromethyl)-1H-imidazo(4,5-b)pyridine is diazotized and subsequently reacted with cuprous cyanide to obtain the corresponding 5,6-dicyano-1-hydroxy-2-(trifluoromethyl)-1H-imidazo(4,5-b)pyridine. It is converted to the corresponding 5,6-dicarboxy compound by treatment with 70 percent sulfuric acid. Subsequent reaction of the 5,6-dicarboxy1-hydroxy-2-(trifluoromethyl)-1H-imidazo(4,5-b)pyridine with SF$_4$ in the presence of HF yields the corresponding 2,5,6-tris(trifluoromethyl)-1-hydroxy-1H-imidazo(4,5-b)pyridine. Rosenmund reduction of the 5,6-bis(difluoromethyl)-1-hydroxy-2-(trifluoromethyl)-1H-imidazo(4,5-b)pyridine. In turn, this compound is chlorinated to obtain 5,6-bis(difluorochloromethyl)-1-hydroxy-2-(trifluoromethyl)-1H-imidazo(4,5-b)pyridine.

6-Amino-5,7-dinitro-1-hydroxy-2-(trifluoromethyl)-1H-imidazo(4,5-b)pyridine is diazotized and the diazo group subsequently removed entirely by reduction with hypophosphorus acid. The resulting 5,7-dinitro-1-hydroxy-2-(trifluoromethyl)-1H-imidazo(4,5-b)pyridine is hydrogenated to the corresponding 5,7-diamino-1-hydroxy-2-(trifluoromethyl)-1H-imidazo(4,5-b)pyridine. This compound is diazotized and subsequently reacted with the sodium salt of methyl mercaptan to obtain 5,7-bis(methylthio)-1-hydroxy-2-(trifluoromethyl)-1H-imidazo(4,5-b)pyridine which is oxidized to the corresponding 5,7-bis(methylsulfonyl)-1-hydroxy-2-(trifluoromethyl)-1H-imidazo(4,5-b)pyridine.

5-Chloro-3-nitro-2-aminopyridine is reacted with 2,2,3,3-tetrafluoropropionyl chloride to yield 5-chloro-3-nitro-2-(2,2,3,3-tetrafluoropropionamido)pyridine, which when hydrogenated yields 6-chloro-1-hydroxy-2-(1,1,2,2-tetrafluoroethyl)-1H-imidazo(4,5-b)pyridine. This compound is reacted with trimethylamine to prepare 6-chloro-1-hydroxy-2-(1,1,2,2-tetrafluoroethyl)-1H-imidazo(4,5-b)pyridine trimethylamine salt.

5-Methyl-3-nitro-2-aminopyridine is reacted with trifluoroacetic anhydride to obtain 5-methyl-3-nitro-2-(trifluoroacetamido)pyridine, which when hydrogenated yields 6-methyl-1-hydroxy-2-(trifluoromethyl)-1H-imidazo(4,5-b)pyridine, m.p., 275°C.

5-(Perfluorooctyl)-3-nitro-2-aminopyridine is reacted with 2,2,3,3-tetrafluoropropionyl chloride to obtain 5-(perfluorooctyl)-3-nitro-2-(2,2,3,3-tetrafluoropropionamido)pyridine, which when hydrogenated yields 6-(perfluorooctyl)-1-hydroxy-2-(1,1,2,2-tetrafluoroethyl)-1H-imidazo(4,5-b)pyridine.

The compounds of the present invention are adapted to be employed as herbicides. The compounds can be utilized to achieve broad herbicidal action; hence, in its broadest sense, the present invention is directed to a method which comprises applying to a plant part, which can be a stem, leaf, flower, fruit, root, or seed or other similar reproductive unit of a plant, a growth-inhibiting amount of one of the substitued-1-hydroxy-2-(1,1-difluoroalkyl)-1H-imidazo(4,5-b)pyridine compounds of the present invention or one of the defined salts thereof. However, the compounds can also be utilized to take advantage of selective patterns of herbicidal activity.

It is not critical to the practice of the present invention that complete destruction of undesirable vegetation be obtained, it being adequate if the growth of the unwanted vegetation is merely inhibited. Especially where selective action is sought, inhibition falling short of actual killing is adequate, particularly when combined with naturally occurring conditions such as limited moisture and the like which more adversely affect the vegetation selectively inhibited than the crop plant.

The compounds of the present invention are suited to a wide variety of herbicidal applications. Thus, for example, at rates which evoke the selective action of the compounds, which rates are defined more completely hereinbelow, the compounds can be used as selective herbicides in crop plants, such as, for example, cotton, corn, sorghum, soybeans, and the like. In such use application can be made preemergent to both crops and weeds, or, preferably by means of a directed spray application technique, postemergent to the crop plant but both preemergent and postemergent to the weeds. In another application, the compounds can be used to give broad herbicidal action on non-crop land, including intermittently non-crop strips of contour-farmed land. For such usage on so-called fallow land, application can be made in spring to suppress vegetative growth until a fall or following spring planting, or in the fall to suppress vegetative growth until a spring or following fall planting. Furthermore, in another application, the present compounds can be utilized to control weeds in tree crop plantings, such as plantings of the various citrus trees. In all of these various applications, and yet others for which the present compounds are suited, another advantage is that the compounds need not be disced into the soil being treated, it being adequate if one of the compounds, or a formulation containing one of the compounds, is merely spread onto the top surface. However, where desired or convenient, the compounds can be disced into, or otherwise mechanically mixed with the soil. In addition to the foregoing terrestrial embodiments, the present compounds can also be utilized as aquatic herbicides.

The practice of the present invention in any of its numerous embodiments can in some instances be carried out with unmodified compound; however, for good results, it is generally necessary that the compound be employed in modified form, that is, as one component of a composition formulated to implement the plant growth-inhibiting effects. Thus, for example, the active agent can be mixed with water or other liquid or liquids, preferably aided by the usage of surface active agent. The active agent can also be incorporated on a finely divided solid, which can be a surface active substance, to yield a wettable powder, which can subsequently be dispersed in water or other liquid, or incorporated as part of a dust which can be applied directly. Other methods of formulatons are known in the art and can be employed in implementing the present invention.

In carrying out the novel method of the present invention, the exact amount of the active agent employed is not critical and will vary, depending upon the type of growth-inhibiting effect desired, the identity of the plants concerned, the particular active agent used, weather conditions, and the like. In general, a broad growth-inhibiting effect is obtained with rates of from 0.5 to 20 pounds or more of active agent per acre, and such rates are suitable and effective for control of vegetative growth on fallo land. When it is desired to obtain a selective growth-inhibiting effect on weeds in areas containing crop plants such as corn, soybeans, and cotton, rates of from 0.25 to 5 pounds generally give good results. When in the typical mode of operation, the active agent is employed as a composition comprising the agent, the exact concentration of active agent in the composition is not critical, except that the concentration and total amount of formulation employed be adequate to supply the appropriate amount of active agent on a per acre basis. In general, good results are obtained when employing formulations containing the active agent in a concentration of from 0.5 to 10 percent or higher, in the instance of a liquid formulation; and in a concentration of from 1.0 to 5.0 percent or higher, in the instance of a dust, powder, granule, or the like. More concentrated formulations can be prepared and are often preferred in that they can serve, depending upon the particular application contemplated and the particular concentration, both as a concentrated formulation for purposes of shipment, storage, and the like, and as an ultimate treating composition. Thus, for example, formulations often preferably contain a surface active agent and the present active agent, the latter being present in an amount of from 0.5 to 99.5 percent, by weight; or an inert, finely divided solid and the present active agent, the latter being present in an amount of from 1.0 to 99.0 percent, by weight. Such formulations, as indicated, can be employed directly in certain applications, but can also be diluted and subsequently employed in many other applications.

Liquid compositions containing the desired amount of active agent are prepared by dissolving the substance in a liquid, with or without the aid of a surface active dispersing agent such as an ionic or non-ionic emulsifying agent. Most preferably, the subject compound in acidic form is dissolved in a dilute aqueous solution of a base, such as, i.e., sodium hydroxide, whereby a water soluble salt is prepared in solution. Although the use of an organic liquid carrier is seldom preferred in view of the foregoing, it can be used in conjunction with a surface active dispersing agent. When so used, suitable such liquids include agricultural spray oils and the petroleum distillates such as diesel fuel, kerosene, fuel oil naphthas and Stoddard solvent. The choice of dispersing and emulsifying agent and the amount thereof employed is dictated by the nature of the composition and by the ability of the agent to facilitate the dispersion of the active agent in the carrier to produce the desired composition. Dispersing and emulsifying agents which can be employed in the compositions include the condensation products of alkylene oxides with phenols and organic acids, alkyl aryl sulfonates, polyoxyalkylene derivatives or sorbitan esters, complex ether alcohols, and the like. Representative surface active agents which are suitably employed in implementing the present invention are identified in U.S. Pat. Nos. 3,095,299, second column, lines 25–36, 2,655,447, column 5, and 2,412,510, columns 4 and 5.

In the preparation of dust compositions, the active ingredient is intimately dispersed in and on a finely divided solid such as clay, talc, chalk, gypsum, limestone, vermiculite fines, perlite, and the like. In one method of achieving such dispersion, the fnely divided carrier is mechanically mixed or ground with the active agent.

Similarly, dust compositions containing the toxicant compounds can be prepared with various of the solid surface active dispersing agents such as bentonite, fuller's earth, attapulgite and other clays. Depending upon the proportions of ingredients, these dust compositions can be employed as concentrates and subsequently diluted with additional solid surface active dispersing agents or with chalk, talc, or gypsum and the like to obtain the desired amount of active ingredient in a composition adapted to be employed for the suppression of the growth of the plants. Also, such dust compositions can be dispersed in water, with or without the aid of a dispersing agent, to form spray mixtures.

Formulations containing the present active agent are often advantageously further modified by incorporation therein of an effective amount of a surfactant which facilitates the dispersion and spreading of the formulation of the plant leaf surfaces and the incorporation of the formulation by the plant.

In accordance with the present invention, the active agent can be dispersed in soil or other growth media in any convenient fashion. Applications can be carried out by simply mixing with the media, by applying to the surface of soil and thereafter dragging or discing into the soil the desired depth, or by employing a liquid carrier to accomplish the penetration and impregnation. The application of spray and dust compositions to the surface of soil, or to plant parts or the above ground surfaces of plants can be carried out by conventional methods, e.g., powder dusters, boom and hand sprayers and spray dusters, whether surface or air-borne. However, while such conventional modes of application can be used, they are not required. As above noted, it is an advantage of the present invention that the compounds serving as active agent are active and effective as herbicides when merely placed on the surface of the soil, without any additional step to assist incorporation. Thus, the compounds are of substantially the same efficacy regardless of whether they are applied to the surface only, or whether they are applied to the surface and subsequently disced into the soil.

In a further method, the distribution of the active agent in soil can be accomplished by introducing the agent into the water employed to irrigate the soil. In such procedures, the amount of water is varied with the porosity and water holding capacity of the soil to obtain a desired depth of distribution of the agent.

In addition, the present method also comprehends the employment of an aerosol composition containing one or more of the present active agents as an active compound. Such a composition is prepared according to conventional methods wherein the agent is dispeersed in a solvent, and the resultant dispersion mixed with a propallant in liquid state. Such variables as the particular agent to be used and the nature of the vegetation which is to be treated will determine the desirability of the solvent and concentration of the agent therein.

EXAMPLE 48:

6-Chloro-1-hydroxy-2-(trifluoromethyl)-1H-imidazo(4,5-b)-pyridine benzylamine salt was prepared as a means of formulation. More praticularly, 1 gram of 6-chloro-1-hydroxy-2-(trifluoromethyl)-1H-imidazo(4,5-b)pyridine was suspended in a about 10 milliliters of water and 1 milliliter of benzylamine was added. The reaction mixture was evaporated, yielding a syrup containing 6-chloro-1-hydroxy-2-(trifluoromethyl)-1H-imidazo(4,5-b) pyridine benzylamine salt. The syrup is useful to be diluted with water to serve, when so diluted, as a spraying composition.

EXAMPLES 49–52:

Various of the compounds to be employed as active agent in accordance with the present invention were evaluated for preemergent application to various species of plants. In this evaluation, a soil was prepared consisting of one part masonry sand and one part shredded top soil blended together in a cement mixer. One gallon of this soil was placed in a 25 × 35 cm. galvanized flat and was patted down with a bench brush until level. A three-row marker was used to make 2 ½ cm. deep furrows in approximately two-fifths of the flat. Crop seeds consisting of four kernels of corn, five cotton seeds and five soybean seeds were placed in these furrows. A four-row template was then placed on the remaining soil and the indicated approximate numbers of each of the following seeds were planted, one species to each section: foxtail (millet), 80–100 seeds;

velvetleaf (40–50 seeds); rough pigweed (150–250 seeds); and large crabgrass (100–150 seeds).

Sufficient soil was added to cover the entire flat. Thus, the weed seeds were covered to a depth of about 6 mm. and the crop seeds were covered to a depth of about 3 cm.

In assaying the effect of the composition as preemergent herbicides, a flat prepared as above, taken either on the day of planting or on the next day, was placed in a chamber equipped with a turntable and an air exhaust. The herbicidal composition, either a spray-type emulsion or a wettable powder, was applied to the flat with a modified DeVilbiss atomizer hooked to an air source. Twelve and one-half milliliters of the composition under test were applied to each flat either on the day of planting or the succeeding day. Injury ratings and observations as to type of injury were made eleven to twelve days after treatment. The injury rating scale used was as follows:

0—no injury
1—sight injury
2—moderate injury
3—severe injury
4—death When more than one determination was carried out at a given rate, an average value was calculated for the injury rating. Each compound elevated was formulated as a spray by one of the following procedures. In one method the particular compound was wetted by grinding in a mortar with one part of polyoxyethylene sorbitan monolaurate. Five hundred parts of water were added slowly to the resultant creamy paste to give an aqueous dispersion with a surfactant concentration of 0.2 percent. This dispersion was entirely satisfactory for spray application. In a second procedure the compound was dissolved in one volume of acetone, and the acetone solution was diluted with nineteen volumes of water containing 0.1 percent of polyoxyethylene sorbitan monolaurate.

In the following table setting forth the results of the evaluation, column 1 gives the name of the compound under test; column 2, the rate in pounds per acre at which the compound was applied to the test flat; and the remaining columns, the injury to the particular plant seeds or seedlings as measured by the foregoing scale.

TABLE 1

Injury Rating on Preemergent Treatment

| Compound | Lbs./Acre | Corn | Cotton | Soybean | Crabgrass | Pigweed | Foxtail | Velvet Leaf |
|---|---|---|---|---|---|---|---|---|
| 6-Chloro-1-hydroxy-2-(trifluoromethyl)-1H-imidazo(4,5-b)pyridine | 8 | 1 | 2 | 1 | 4 | 4 | 3 | 3 |
|  | 4 | 1 | 0 | 0 | 4 | 4 | 3 | 4 |
|  | 2 | 0 | 0 | 0 | 3 | 4 | 3 | 4 |
|  | 1 | 0 | 0 | 0 | 4 | 4 | 3 | 2 |
| 2,6-Bis(trifluoromethyl)-1-hydroxy-1H-imidazo-(4,5-b)pyridine | 8 | 3 | 4 | 3 | 4 | — | 4 | — |
| 6-(Methylsulfonyl)-1-hydroxy-2-(trifluoromethyl)-1H-imidazo-(4,5-b)pyridine | 2* | 0 | 0 | 2 | 2 | 3 | 2 | 2 |
| 5-chloro-1-hydroxy-2-(trifluoromethyl)-1H-imidazo(4,5-b)pyridine | 8 | 1 | — | — | 3 | 3 | 4 | — |
|  | 2 | 0 | 0 | 0 | 3 | 3 | 2 | — |

*Not tested at higher rates.

EXAMPLES 53–58:

Representative compounds of the present invention were evaluated for postemergent application to plants including corn and several weed species. The evaluation was carried out in accordance with the procedures of Examples 49–52 except that the test solutions were applied about 9–12 days after the preparation and seeding of the flats. The results are as set forth in the following table:

TABLE 2

Injury Rating on Postemergent Treatment

| Compound | Lbs./Acre | Corn | Cotton | Soybean | Crabgrass | Pigweed | Foxtail | Velvet leaf |
|---|---|---|---|---|---|---|---|---|
| 2,6-Bis(trifluoromethyl)-1-hydroxy-1H-imidazo(4,5-b)-pyridine | 8 | 4 | 4 | 4 | 4 | 4 | 4 | 4 |
|  | 4 | 4 | 4 | 4 | 4 | 4 | 4 | 4 |
|  | 2 | 4 | 4 | 4 | 4 | 4 | 4 | 4 |
|  | 1 | 1 | 4 | 4 | 4 | 4 | 4 | 4 |
| 6-Methylsulfonyl-1-hydroxy-2-(trifluoromethyl-1H-imidazo-(4,5-b)pyridine | 2* | 2 | 4 | 4 | 2 | 4 | 4 | — |
|  | 1 | 1 | 3 | 3 | 2 | 3 | 4 | — |
| 7-Chloro-1-hydroxy-2-trifluoromethyl-1H-imidazo(4,5-b)pyridine | 8 | 1 | — | — | 2 | 3 | 3 | — |
|  | 4 | 0 | — | — | 1 | 3 | 1 | — |
| 6-Methyl-1-hydroxy-2-(trifluoromethyl)-1H-imidazo(4,5-b)pyridine | 8 | 1 | — | — | 3 | 3 | 3 | 1 |
| 5,7-Dibromo-6-amino-1-hydroxy-2-(trifluoromethyl)-1H-imidazo(4,5-b)-pyridine | 8 | 1 | — | — | 3 | 3 | 3 | 3 |
| 5,7-Dibromo-6-chloro-1-hydroxy-2-(trifluoro- | 8 | 1 | — | — | 4 | 4 | 4 | 3 |

TABLE 2-continued

| Compound | Injury Rating on Postemergent Treatment | | | | | | | |
|---|---|---|---|---|---|---|---|---|
| | Lbs./Acre | Corn | Cotton | Soybean | Crabgrass | Pigweed | Foxtail | Velvet leaf |
| methyl)-1H-imidazo(4,5-b)-pyridine | | | | | | | | |

*Not tested at higher rates.

As the foregoing examples illustrate, the compounds of the present invention are effective herbicides. However, satisfactory results are also obtained when the active agent of the present invention, or a composition comprising such active agent, is combined with other agricultural materials intended to be applied to plants, plant parts, or their habitats. Such materials include fertilizers, fungicides, nematocides, insecticides, other herbicides, soil conditioning agents, and the like.

EXAMPLES 59–60:

6-Chloro-1-hydroxy-2-(trifluoromethyl)-1H-imidazo(4,5,-b)-pyridine was evaluated in combination with 2-chloro- 4-ethylamino-6-isopropylamino-s-triazine and separately in combination with 2-chloro-2',6'-diethyl-N-(methoxymethyl)acetanilide for the control of plants. The evaluations were conducted as described in Examples 49–52, except that the rates of compound differed and the species were different. The results were as set forth in the following tables. General herbicidal effect was rated on a scale of 0–10, with 0 = no injury and 10 = death. Observations were also made for the following other specific phytotoxic effects.

A = Abscission of leaves
B = Burned
C = Chlorosis
D = Death
E = Epinasty
F = Formative effects other than epinasty
G = Dark green
I = Increased plant growth
L = Local necrosis
N = No germination
P = Purple pigmentation
R = Reduced germination
S = Stunting
U = Unclassified injury Where noted, such effects were recorded and also reported in the following tables.

TABLE 3

| Compound | Rates Lbs./A | Jimsonweed | Lambs Quarter | Velvet-leaf | Corn | Ragweed | Pigweed | Morning glory | Johnson Grass | Sorghum | Foxtail Millet | Corn | Large Crabgrass | Rice | Barnyard Grass |
|---|---|---|---|---|---|---|---|---|---|---|---|---|---|---|---|
| A | 0.25 | 4B | 5S | 0 | 0 | 2S | 0 | 10D | 2S | 0 | 0 | 0 | 2S | 0 | 0 |
| | 0.5 | 8BS | 6S | 2S | 0 | 6S | 2S | 10D | 2S | 3SB | 2S | 0 | 2S | 3B | 3S |
| | 1.0 | 9BS | 9SB | 8BS | 0 | 8BS | 6S | 10D | 8BS | 8BS | 7SB | 0 | 3S | 6B | 3S |
| | 2.0 | 9BS | 9BS | 10D | 3SB | 8BS | 6SB | 10D | 8BS | 10D | 10D | 3SB | 9BS | 9B | 9BS |
| B | 0.25 | 9BS | 9BS | 3S | 0 | 5S | 9BS | 8BS | 3S | 0 | 0 | 0 | 0 | 4B | 2S |
| | 0.5 | 9BS | 9BS | 3S | 0 | 7SB | 10D | 9BS | 0 | 0 | 0 | 0 | 2S | 4B | 5SB |
| | 1.0 | 9BS | 9.5BS | 7BS | 0 | 8BS | 10D | 10D | 0 | 1B | 4SB | 0 | 5S | 7B | 4SB |
| | 2.0 | 9BS | 9.5BS | 10D | 0 | 10D | 10D | 10D | 2S | 2B | 5SB | 0 | 6BS | 8B | 8BS |
| A + B | 0.25+0.25 | 9BS | 9BS | 6BS | 0 | 7BS | 8BS | 9BS | 7SB | 3S | 2S | 0 | 2S | 7B | 6BS |
| | 0.25+0.5 | 9BS | 9BS | 7BS | 0 | 10D | 10D | 10D | 3S | 0 | 2S | 0 | 4S | 5B | 7BS |
| | 0.25+1.0 | 10D | 9.5BS | 10D | 0 | 9BS | 10D | 10D | 3S | 2S | 7SB | 0 | 6S | 9B | 9BS |
| | 0.25+2.0 | 9BS | 9BS | 10D | 0 | 10D | 10D | 10D | 4SB | 5SB | 8BS | 0 | 9BS | 10D | 9.5BS |
| A + B | 0.5+0.25 | 9BS | 9BS | 9.5BS | 0 | 9S | 10D | 10D | 2SB | 3BS | 4SB | 0 | 2S | 8B | 6BS |
| | 0.5+0.5 | 9BS | 9BS | 9BS | 0 | 10D | 10D | 10D | 3S | 3SB | 4S | 0 | 4S | 8B | 9BS |
| | 0.5+1.0 | 9.5BS | 9BS | 9.5BS | 0 | 10D | 10D | 10D | 4SB | 4S | 5S | 0 | 5S | 8B | 9BS |
| | 0.5+2.0 | 9.5BS | 9S | 10D | 0 | 10D | 10D | 10D | 8BS | 5SB | 8BS | 0 | 9BS | 10D | 10D |
| A + B | 1.0+0.25 | 9.5BS | 9SB | 9.5BS | 2S | 9.5BS | 9SB | 10D | 9BS | 9BS | 10D | 2S | 5SB | 10D | 4SB |
| | 1.0+0.5 | 9BS | 10D | 9.8BS | 0 | 9.5BS | 9.5BS | 10D | 10D | 8BS | 7BS | 0 | 6SB | 10D | 9BS |
| | 1.0+1.0 | 10D | 10D | 9.5BS | 1S | 10D | 10D | 10D | 8BS | 9BS | 10D | 0 | 9BS | 10D | 9.5BS |
| | 1.0+2.0 | 9BS | 9SB | 10D | 2S | 10D | 10D | 10D | 9.5BS | 10D | 10D | 1S | 7SB | 10D | 9.5BS |
| A + B | 2.0+0.25 | 10D | 9.5SB | 9.8BS | 3S | 10D | 9.5BS | 10D | 9.5BS | 10D | 10D | 2S | 9.5BS | 10D | 9.5BS |
| | 2.0+0.5 | 10D | 9SB | 10D | 4S | 10D | 10D | 10D | 9SB | 10D | 10D | 4S | 9SB | 10D | 9.5BS |
| | 2.0+1.0 | 9.8BS | 10D | 9.5BS | 4S | 10D | 10D | 10D | 9.5BS | 10D | 10D | 3S | 10D | 10D | 10D |
| | 2.0+2.0 | 10D | 10D | 10D | 4S | 10D | 10D | 10D | 9.5BS | 9.8BS | 10D | 2S | 9.5BS | 10D | 10D |
| (Control) | 0 | 0 | 0 | 0 | 0 | 0 | 0 | 0 | 0 | 0 | 0 | 0 | 0 | 0 | 0 |

A = 6-chloro-1-hydroxy-2-(trifluoromethyl)-1H-imidazo(4,5-b)pyridine
B = 2-chloro-4-ethylamino-6-isopropylamino-s-triazine

TABLE 4

| Compound | Rates Lbs./A | Jimson-weed | Lambs Quarter | Velvet-leaf | Corn | Rag-weed | Pig-weed | Morning glory | Johnson Grass | Sorghum | Foxtail Millet | Corn | Large Crabgrass | Rice | Barnyard Grass |
|---|---|---|---|---|---|---|---|---|---|---|---|---|---|---|---|
| A | 0.25 | 2B | 7RS | 0 | 0 | 3S | 0 | 5SB | 0 | 0 | 0 | 0 | 0 | 0 | 0 |
|   | 0.5 | 5BS | 6SB | 3S | 0 | 2S | 3S | 10D | 0 | 4S | 2S | 0 | 0 | 3B | 0 |
|   | 1.0 | 9BS | 6SB | 5SB | 0 | 8BS | 2S | 10D | 7SB | 8BS | 6BS | 0 | 2S | 4SB | 2S |
|   | 2.0 | 9BS | 8BS | 9.5BS | 2S | 10D | 6BS | 10D | 10D | 10D | 10D | 3S | 7SB | 8BS | 9BS |
| C | 0.5 | 0 | — | 2S | 0 | 0 | 7S | 0 | 9RS | 3SF | 9SBR | 0 | 8RS | 0 | 5SR |
|   | 1.0 | 3S | 5S | 3S | 0 | 5S | 8SR | 2S | 9RS | 4SF | 9RSB | 0 | 9RS | 9RS | 8S |
|   | 2.0 | 4S | 10N | 6S | 2S | 7S | 10N | 2SF | 9.5RS | 8SF | 9.5RSB | 1SB | 10N | 10N | 8RSF |
|   | 4.0 | 5S | 10N | 3S | 2S | 8SR | 10N | 3SF | 10N | 8SFR | 10D | 2S | 10N | 10N | 9.5RS |
| A+C | 0.25+0.5 | 8BS | 7RS | 2S | 0 | 3S | 9RS | 10D | 9.5RS | 4SF | 9.5BS | 0 | 9.5RS | 5S | 9RS |
|   | 0.25+1.0 | 9BS | 10N | 4S | 0 | 7SR | 10N | 9BS | 10D | 6SF | 9.5BS | 0 | 10N | 10N | 9.5RS |
|   | 0.25+2.0 | 9BS | 10N | 5S | 2S | 10N | 10N | 9BS | 10D | 7SF | 10D | 0 | 10D | 9.5RS | 9.5RS |
|   | 0.25+4.0 | 10D | 10D | 6S | 2S | 10D | 10N | 10D | 10D | 9SF | 10D | 1S | 10N | 10N | 10N |
| A+C | 0.5+0.5 | 9BS | 9.5RS | 2S | 0 | 8RS | 10N | 10D | 10D | 5SF | 10D | 0 | 9.8RS | 6SR | 9RS |
|   | 0.5+1.0 | 9BS | 10N | 5SB | 1S | 5S | 10N | 10D | 10D | 8SF | 10D | 0 | 9RS | 9.5RS | 9.5RS |
|   | 0.5+2.0 | 9.5BS | 10N | 6SB | 1S | 10N | 10N | 10D | 10D | 9SF | 10D | 0 | 10N | 10N | 9.8RS |
|   | 0.5+4.0 | 10D | 10N | 7SB | 3S | 10N | 10N | 10D | 10D | 9.5SF | 10D | 1S | 10N | 10N | 9.8RS |
| A+C | 1.0+0.5 | 8BS | 7SF | 8BS | 1S | 7S | 10N | 10D | 10D | 8BSF | 10D | 0 | 8SB | 7SB | 10D |
|   | 1.0+1.0 | 9.5BS | 7S | 7BS | 1S | 8SB | 10D | 10D | 10D | 8SBF | 10D | 0 | 9SB | 9.5RS | 9.5BS |
|   | 1.0+2.0 | 9.5BS | 8SR | 9BS | 2S | 10D | 10N | 10D | 10N | 9BSF | 10D | 1SB | 10D | 10D | 10D |
|   | 1.0+4.0 | 9.5BS | 10D | 9.5BS | 4S | 10D | 10D | 10D | 10D | 9.5BS | 10D | 4SB | 10D | 10N | 10D |
| A+C | 2.0+0.5 | 9.5BS | 9RS | 9.5BS | 5SB | 9S | 10N | 10D | 10D | 10D | 10D | 3S | 10D | 8BS | 10D |
|   | 2.0+1.0 | 9.5BS | 10D | 10D | 4SB | 10D | 10D | 10D | 10D | 10D | 10D | 5S | 9.5BS | 9RS | 9.5BS |
|   | 2.0+2.0 | 9.8BS | 10D | 10D | 4 SBC | 10D | 10D | 10D | 10D | 8BS | 10D | 3S | 10D | 9.5RS | 10D |
|   | 2.0+4.0 | 10D | 10D | 10D | 3S | 10D | 10N | 10D | 10D | 9.8BS | 10D | 4S | 10D | 10N | 9.8BS |
| (Control) | 0 | 0 | 0 | 0 | 0 | 0 | 0 | 0 | 0 | 0 | 0 | 0 | 0 | 0 | 0 |

A = 6-chloro-1-hydroxy-2-(trifluoromethyl)-1H-imidazo(4,5-b)pyridine
C = 2-chloro-2',6'-diethyl-N-(methoxymethyl)acetanilide Essentially the same results as those reported in foregoing Examples 49–60 are obtained when evaluating the other representative compounds of the present invention identified in Examples 1–48.

The substituted-3-nitro-2-aminopyridine which are employed as starting materials in the first synthetic route:

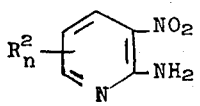

are in general prepared by known procedures. Most typically, the compounds are prepared by nitration, in standard procedures, of suitably substituted pyridines which are known or are prepared in procedures readily available to those skilled in the art. Thus, for example, in synthesizing 5-(difluorochloromethyl)-2-amino-pyridine, a 2-aminoformylpyridine:

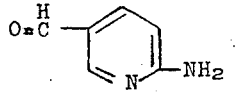

is reacted with SF$_4$ to obtain 5-(difluoromethyl)-2-aminopyridine; this compound, in turn, can be chlorinated to obtain the corresponding 5-(difluorochloromethyl)-2-aminopyridine. The 5-(trifluoromethyl)2-aminopyridine is synthesized by treatment of 5-carboxy-2-hydroxypyridine with SF$_4$ in the presence of HF, to yield 5-(trifluoromethyl)-6-fluoro-5,6-dihydro-2-hydroxypyridine, which, on treatment with sodium hydroxide, yields 5-(trifluoromethyl)-2-hydroxypyridine. The hydroxy moiety of this compound can be converted in standard procedures to an amino group, thus yielding the desired 5-(trifluoromethyl)-2-aminopyridine compound.

Preferred starting materials for utilization in the first synthetic route are the mono-substituted 3-nitro-2-aminopyridines.

Those substituted-3-nitro-2-aminopyridine compounds wherein the substituent is alkylsulfonyl:

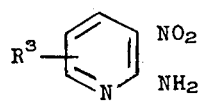

are prepared in accordance with the following reaction scheme: for the sake of simplicity, the scheme is shown for the preparation of a 5-alkylsulfonyl compound, only.

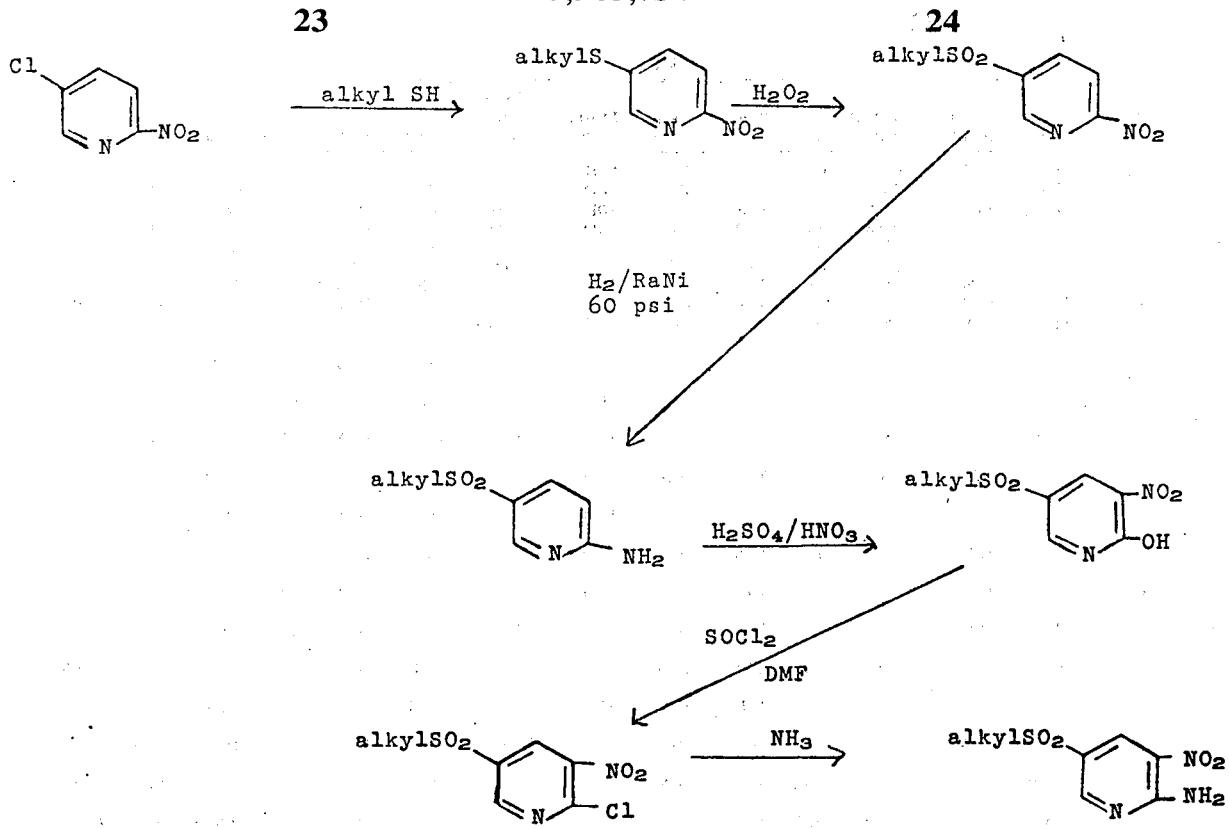

The following example illustrates the preparation of the (alkylsulfonyl)-3-nitro-2-aminopyridine compounds.

EXAMPLE 61:
5-(METHYLSULFONYL)-3-NITRO-2-AMINOPYRIDINE

5-Chloro-2-nitropyridine (8.0 grams) was added to a solution of 2.5 grams of sodium methanethiolate in 100 milliliters of ethanol at a temperature of 0°C. to which solution excess sodium methanethiolate was added portionwise. The resulting reaction mixture was then heated to reflux and refluxed for 15 hours with constant stirring. At the end of the 15 hours, the reaction mixture was filtered and allowed to concentrate to 75 milliliters. The reaction mixture was then permitted to cool and filtered again, yielding the desired 5-(methylthio)-2-nitropyridine; it was recrystallized from ethanol, m.p., 100.5–02.5°C.

To 3.4 grams of the 5-(methylthio)-2-nitropyridine in 50 milliliters of glacial acetic acid there was added 23.8 grams of 30 percent hydrogen peroxide. The resulting reaction mixture was stirred for 60 hours at 25°C., then poured over ice and filtered to separate the desired 5-(methylsulfonyl)-2-nitropyridine product, which, after recrystallization from ethanol/acetone, melted at 165°–7°C.

The entire yield of 5-(methylsulfonyl)-2-nitropyridine (3.2 grams) was dissolved in about 100 milliliters of acetone and 1 teaspoon of Raney nickel slurry in ethanol added. The mixture was then shaken on a Parr hydrogenator for 15 hours at 60 p.s.i. Thereafter, the mixture was filtered and solvent evaporated, yielding the desired 5-(methylsulfonyl)-2-aminopyridine product. It was mixed with hot water containing some charcoal, filtered and the mixture then cooled to 25°C. The resulting solid was crystallized from benzene/acetone, m.p., 132°–34°C.

5-(methylsulfonyl)-2-aminopyridine (1.0 gram) was dissolved in 10 milliliters of concentrated sulfuric acid and 2.0 milliliters of fuming nitric acid added dropwise with stirring, and the resulting reaction mixture stirred an additional 10 minutes, warmed on a steam bath for 10 minutes, and allowed to stir at 25°C. for 15 hours. The reaction mixture was then poured over ice with stirring. Precipitation occurred, and the mixture was filtered to separate 5-(methylsulfonyl)-3-nitro-2-hydroxypyridine; it was washed with water and recrystallized from ethanol/acetone, m.p., 229°–32°C.

5-(Methylsulfonyl)-3-nitro-2-hydroxypyridine (2.0 grams) was mixed with 25 milliliters of thionyl chloride and 1 milliliter of dimethylformamide and the mixture refluxed for 2 hours. The reaction mixture was then evaporated to separate 5-(methylsulfonyl)-3-nitro-2-chloropyridine. It was shaken with water to remove any traces of thionyl chloride, and then filtered and mixed with 50 milliliters of ammonium hydroxide. This mixture was stirred, at room temperature, for 15 hours, then poured into ice water and filtered to separate 5-(methylsulfonyl)-3-nitro-2-aminopyridine. It was recrystallized from ethanol/acetone, m.p., 239°–41°C.

Analysis, Calc.: C, 33.19; H, 3.25; N, 19.35.
Found: C, 33.32; H, 3.31; N, 19.18.

In like manner are prepared the other (alkylsulfonyl)-3-nitro-2-aminopyridine compounds:
  6-(ethylsulfonyl)-3-nitro-2-aminopyridine;
  5-(isopropylsulfonyl)-3-nitro-2-aminopyridine;
  4-(n-propylsulfonyl)-3-nitro-2-aminopyridine;

5-(n-butylsulfonyl)-3-nitro-2-aminopyridine;
6-(isobutylsulfonyl)-3-nitro-2-aminopyridine;
5-(sec-butylsulfonyl)-3-nitro-2-aminopyridine; and
5-(tert-butylsulfonyl)-3-nitro-2-aminopyridine.

Intermediates in the preparation of these compounds include the following:

6-(ethylthio)-2-nitropyridine
5-(n-butylthio)-2-nitropyridine
4-(n-propylsulfonyl)-2-nitropyridine
5-(isobutylsulfonyl)-2-aminopyridine
6-(isopropylsulfonyl)-3-nitro-2-hydroxypyridine
5-(sec-butylsulfonyl)-3-nitro-2-chloropyridine
6(ethylsulfonyl)-3-nitro-2-chloropyridine
5-(tert-butylsulfonyl)-3-nitro-2-aminopyridine
6-(ethylsulfonyl)-3-nitro-2-aminopyridine Preferred compounds of the present invention are those mono-substituted compounds of the formula

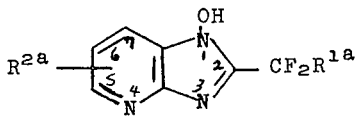

wherein $R^{1a}$ represents hydrogen, chlorine, fluorine, difluoromethyl, or trifluoromethyl, and $R^{2a}$ represents halogen, nitro, —$CF_3$, —$CF_2Cl$, —$CF_2H$, or loweralkylsulfonyl of $C_1$–$C_4$. Yet more preferred compounds are those of the foregoing formula wherein the $R^{2a}$ substituent is located at the 6-position, i.e., compounds of the formula

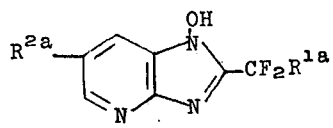

wherein $R^{1a}$ and $R^{2a}$ are as above defined.

We claim:

1. A compound selected from the group consisting of the compounds of the formula

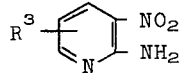

wherein $R^3$ represents loweralkylsulfonyl of $C_1$–$C_4$.

2. A compound of claim 1 wherein $R^3$ is at the 5-position.

3. The compound of claim 2 which is 5-(methylsulfonyl)-3-nitro-2-aminopyridine.

4. The compound of claim 2 which is 5-(ethylsulfonyl)-3-nitro-2-aminopyridine.

5. The compound of claim 2 which is 5-(n-butylsulfonyl)-3-nitro-2-aminopyridine.

* * * * *